(12) United States Patent
Miller et al.

(10) Patent No.: US 11,129,641 B2
(45) Date of Patent: Sep. 28, 2021

(54) MECHANICAL RESECTION INSTRUMENTS WITH OUTFLOW CONTROL AND RELATED METHODS

(71) Applicant: Smith & Nephew, Inc., Memphis, TN (US)

(72) Inventors: David J. Miller, Austin, TX (US); Jean Woloszko, Austin, TX (US); Jonathan L. Gaspredes, Austin, TX (US); Rajitha Aluru, Austin, TX (US)

(73) Assignee: SMITH & NEPHEW, INC., Memphis, TN (US)

( * ) Notice: Subject to any disclaimer, the term of this patent is extended or adjusted under 35 U.S.C. 154(b) by 180 days.

(21) Appl. No.: 16/487,371

(22) PCT Filed: Mar. 14, 2018

(86) PCT No.: PCT/US2018/022339
§ 371 (c)(1),
(2) Date: Aug. 20, 2019

(87) PCT Pub. No.: WO2018/170063
PCT Pub. Date: Sep. 20, 2018

(65) Prior Publication Data
US 2020/0054356 A1     Feb. 20, 2020

Related U.S. Application Data

(60) Provisional application No. 62/482,528, filed on Apr. 6, 2017, provisional application No. 62/472,293, filed on Mar. 16, 2017.

(51) Int. Cl.
*A61B 17/3207* (2006.01)
*A61B 90/98* (2016.01)
(Continued)

(52) U.S. Cl.
CPC ...... *A61B 17/320758* (2013.01); *A61B 90/98* (2016.02); *A61B 17/32002* (2013.01);
(Continued)

(58) Field of Classification Search
CPC ........ A61B 2217/005; A61B 2217/007; A61B 2017/00026; A61B 2017/00035;
(Continued)

(56) References Cited

U.S. PATENT DOCUMENTS 5,334,211 A      8/1994 Shiber
5,472,447 A  *  12/1995 Abrams ............. A61B 17/3476
                                                      606/169
(Continued)

FOREIGN PATENT DOCUMENTS

WO       2015175484 A1    11/2015

OTHER PUBLICATIONS

Stryker Corporation; "Innovation Through Integration, Cross Flow Integrated Arthroscopy Pump"; Product Brochure, Copyright 2013 Stryker; 3 pages.
(Continued)

*Primary Examiner* — Katherine H Schwiker
*Assistant Examiner* — Raihan R Khandker

(57) ABSTRACT

Mechanical resection instruments with outflow control. At least some of the example embodiments are methods including: receiving an indication of a first rotational mode of a mechanical resection instrument coupled to a motor of a motor drive unit (MDU); controlling rotation of the rotating portion of the mechanical resection instrument by controlling the motor, the controlling in conformance with the indication of the first rotational mode; setting a first outflow rate through the mechanical resection instrument based on the indication of the first rotational mode; drawing fluid through the mechanical resection instrument at the first
(Continued)

outflow rate during a surgical procedure, the drawing by way of the pump controlled by the controller; sensing a parameter indicative of resection by the mechanical resection instrument; and changing a rate at which fluid is drawn through the mechanical resection instrument, the changing relative to the first outflow rate.

8 Claims, 7 Drawing Sheets

(51) Int. Cl.
    *A61B 17/32*     (2006.01)
    *A61B 17/00*     (2006.01)

(52) U.S. Cl.
    CPC .............. *A61B 2017/00026* (2013.01); *A61B 2017/00035* (2013.01); *A61B 2017/00084* (2013.01); *A61B 2017/00106* (2013.01); *A61B 2017/320004* (2013.01); *A61B 2217/005* (2013.01); *A61B 2217/007* (2013.01)

(58) Field of Classification Search
    CPC ........... A61B 2017/00084; A61B 2017/00106; A61B 2017/00022; A61B 2017/00017; A61B 90/98; A61B 90/90; A61B 17/320016; A61B 17/32002; A61B 17/3207; A61B 17/320708; A61B 17/320725; A61B 17/32075; A61B 17/320758; A61B 17/320786; A61B 2017/320024–320032; A61B 2017/320716; A61B 2017/320733; A61B 2017/320741; A61B 2017/320766; A61B 2017/320775; A61B 2017/320791

See application file for complete search history.

(56) References Cited

U.S. PATENT DOCUMENTS

| | | | |
|---|---|---|---|
| 5,951,581 A * | 9/1999 | Saadat | ........... A61B 17/320758 606/170 |
| 7,510,542 B2 | 3/2009 | Blight | |
| 7,682,333 B2 * | 3/2010 | Deng | ............... A61B 17/32002 604/35 |
| 9,289,110 B2 | 3/2016 | Woolford et al. | |
| 2013/0267892 A1 | 10/2013 | Woolford | |
| 2013/0267894 A1 * | 10/2013 | Woolford | ............. A61B 18/148 604/67 |
| 2014/0140815 A1 * | 5/2014 | Shener-Irmakoglu | ....................... F04D 13/02 415/73 |
| 2014/0257269 A1 | 9/2014 | Woloszko et al. | |
| 2014/0303551 A1 | 10/2014 | Germain et al. | |
| 2016/0302823 A1 * | 10/2016 | Nguyen | ......... A61B 17/320758 |
| 2017/0049952 A1 | 2/2017 | Jezierski et al. | |
| 2017/0224370 A1 | 8/2017 | Loreth | |

OTHER PUBLICATIONS

European Patent Office as Searching Authority; Search Report and Written Opinion dated Jun. 6, 2018 for International patent application PCT/US2018/022339 dated Mar. 14, 2018, 13 pages.

* cited by examiner

MECHANICAL RESECTION INSTRUMENTS WITH OUTFLOW CONTROL AND RELATED METHODS

CROSS-REFERENCE TO RELATED APPLICATIONS

This application is a U.S. National Phase Entry of PCT Application Serial No. PCT/US2018/022339 filed Mar. 14, 2018 and titled "Mechanical Resection Instruments with Outflow Control and Related Methods." The PCT application claims the benefit of U.S. Provisional Application Ser. No. 62/482,528 filed Apr. 6, 2017 titled "Resection Device with Outflow Control," and U.S. Provisional Application Ser. No. 62/472,293 filed Mar. 16, 2017 titled "Mechanical Resection Hand Piece with Suction Lever Overdrive." The PCT application and the provisional applications are incorporated by reference herein as if reproduced in full below.

BACKGROUND

Arthroscopic surgical procedures use a mechanical blade or burr to remove tissue by cutting, scraping, and/or grinding. Related-art mechanical resection devices may use suction to remove debris that is generated by the resection, and in the case of blade-type devices the suction may also pull the tissue into the cutting zone to improve resection efficiency. Suction is controlled in related-art devices by a valve within the hand piece containing the motor, the valve connected to an externally accessible lever. That is, suction is controlled in related-art devices by the surgeon modulating position of a lever associated with the valve.

BRIEF DESCRIPTION OF THE DRAWINGS

For a detailed description of example embodiments, reference will now be made to the accompanying drawings (not necessarily to scale) in which.

DEFINITIONS

Figure 1:
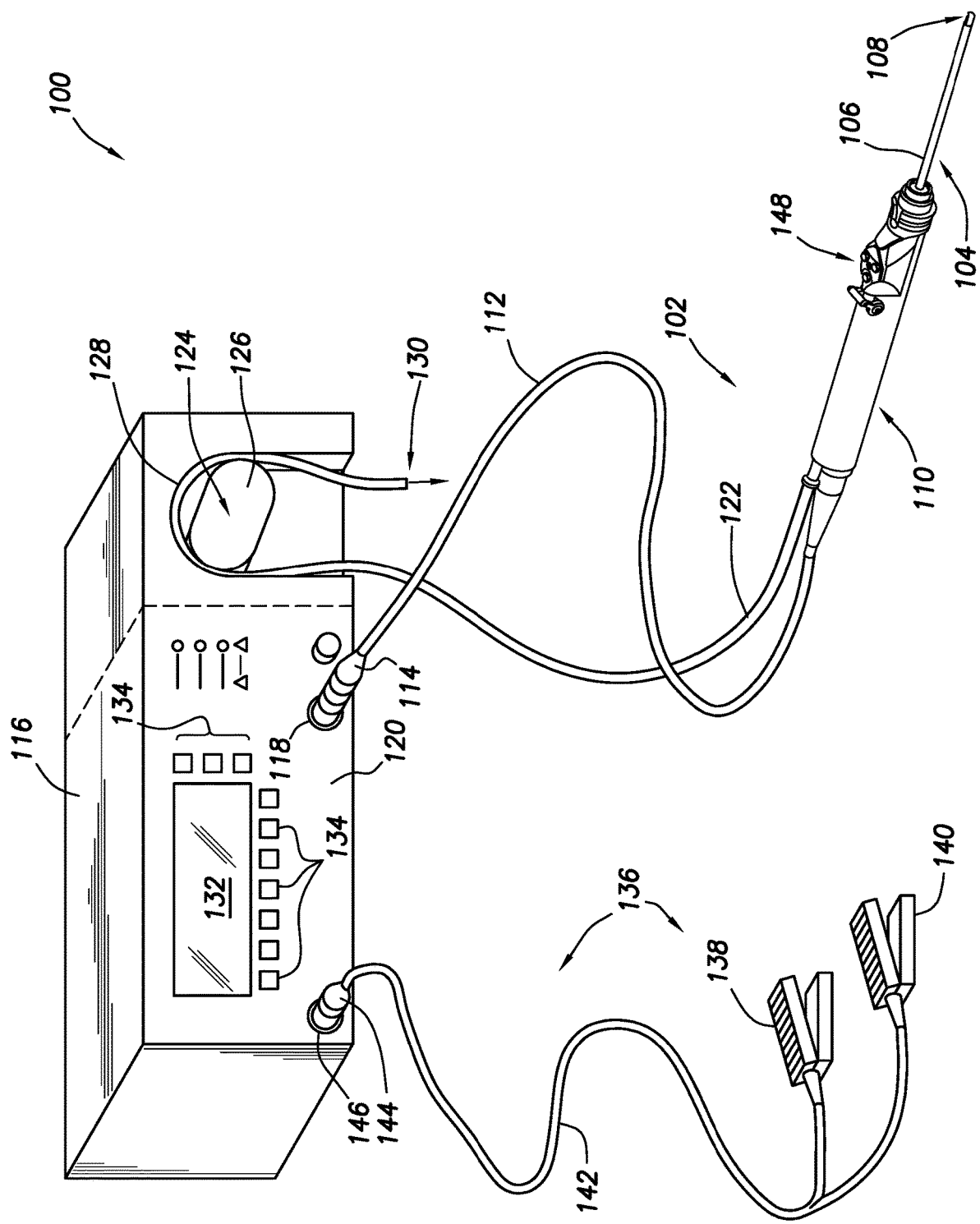
FIG. 1 shows a resection system in accordance with at least some embodiments.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

"Resection byproducts" shall mean individually and collectively blood and tissue fragments (including bone fragments).

"Mechanical resection instrument" shall mean an instrument that removes tissue (including bone) by way of cutting, scraping, and/or grinding. Instruments that remove tissue electrically (i.e., by flowing electrical current through the tissue to desiccate the tissue, or by exposing the tissue to plasma) shall not be considered to be mechanical resection instruments.

"Parameter indicative of resection" shall mean a parameter that directly or indirectly indicates actual use of a mechanical resection instrument to resect tissue (including bone). Movement of a rotating portion alone is not indicative of resection, as the rotating portion can be rotating, and yet the cutting, scraping, and/or grinding component not be in contact with tissue for purposes of resection.

"Control system" shall comprise a field programmable gate array (FPGA), application specific integrated circuit (ASIC), programmable logic device (PLD), programmable logic controller (PLC), microcontroller, specifically implemented processor-based system, or combinations thereof configured to read electrical signals and take control actions responsive to such signals.

The terms "input" and "output" used as nouns refer to connections (e.g., electrical, software), and shall not be read as verbs requiring action. For example, a process control block may have a set point input, a feedback input, a feed-forward input, and a speed control output. In systems implemented directly in hardware, these "inputs" and "outputs" define electrical connections. In systems implemented in software these "inputs" and "outputs" define parameters read by or written by, respectively, the instructions implementing the control block.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various embodiments are directed to mechanical resection systems with outflow control. More particularly, various embodiments are directed to systems comprising a controller, a hand piece referred to as a motor drive unit (MDU), a fluid pump, and a mechanical resection instrument coupled to the MDU. The controller controls the rotating portion of the mechanical resection instrument by way of the motor in the MDU, and the controlling in one of various rotational modes (e.g., forward rotation, reverse rotation, oscillation). While maintaining the rotational mode, the controller modulates outflow rate through the mechanical resection instrument to improve performance. More particularly still, in example embodiments the controller sets an outflow rate based on the rotational mode selected, and the controller increases outflow through the mechanical resection instrument based on parameters that indicate that the mechanical resection instrument is in use resecting tissue (including bone). Further still, in example embodiments the controller increases flow through the mechanical resection instrument proportional to how active the mechanical resection instrument is in resecting tissue. The specification first turns to an example system to orient the reader.

FIG. 1 shows a resection system in accordance with at least some embodiments. In particular, the resection system 100 comprises a wand 102. The wand 102 includes a mechanical resection instrument 104 that comprises an elongate shaft 106 that defines distal end 108. Further, the wand 102 comprises a hand piece or MDU 110 where a physician grips the wand 102 during surgical procedures. The wand 102 further comprises a flexible multi-conductor cable 112 housing one or more electrical leads (not specifically shown in FIG. 1), and the flexible multi-conductor cable 112 terminates in a wand connector 114. As shown in FIG. 1, the wand 102 couples to a shaver controller 116, such as by a controller connector 118 on an outer surface of the enclosure 120 (in the illustrative case of FIG. 1, the front surface of the enclosure 120).

Though not visible in the view of FIG. 1, in some embodiments the wand 102 has one or more internal aspiration channels or fluid conduits. The internal fluid conduit of the wand 102 couples to flexible tubular member 122 used to provide suction or aspiration at the distal end 108 of the wand 102. In accordance with example embodiments, the flexible tubular member 122 couples to a peristaltic pump 124, which peristaltic pump 124 is illustratively shown as an integral component with the shaver controller 116 (i.e., residing at least partially within the enclosure 120 of the shaver controller 116). In other embodiments, an enclosure for the peristaltic pump 124 may be separate from the enclosure 120 for the shaver controller 116 (as shown by dashed lines in the figure), but in any event the peristaltic pump 124 is operatively coupled to the shaver controller 116.

The peristaltic pump 124 comprises a rotor portion 126 (hereafter just "rotor 126") as well as a stator portion 128 (hereafter just "stator 128"). The flexible tubular member 122 couples within the peristaltic pump 124 between the rotor 126 and the stator 128, and movement of the rotor 126 against the flexible tubular member 122 causes fluid movement toward the discharge 130. While the illustrative peristaltic pump 124 is shown with a two-head rotor 126, other types of peristaltic pumps 124 may be used (e.g., a five-head peristaltic pump). In the context of the various embodiments, the peristaltic pump 124 creates a volume-controlled aspiration from a cavity or surgical field at the distal end 108 of the wand 102 (the surgical field not specifically shown), with the outflow rate based on a speed of the rotor 126, as commanded by the shaver controller 116.

Still referring to FIG. 1, a display device or interface device 132 is visible through the enclosure 120 of the shaver controller 116, and in some embodiments a user may select operational modes of the shaver controller 116 by way of the interface device 132 and related buttons 134. For example, using one or more of the buttons 134 the surgeon may select a rotational mode of the rotating portion of the mechanical resection instrument 104 (the rotating portion discussed more below). As another example, using one or more of the buttons 134 the surgeon may select an aggressiveness of the outflow control through the wand 102.

In some embodiments the resection system 100 also comprises a foot pedal assembly 136. The foot pedal assembly 136 may comprise one or more foot pedal devices 138 and 140, a flexible multi-conductor cable 142, and a pedal connector 144. While only two foot pedal devices 138 and 140 are shown, one or more pedal devices may be implemented. The enclosure 120 of the shaver controller 116 may comprise a corresponding connector 146 that couples to the pedal connector 144. A surgeon may use the foot pedal assembly 136 to control various aspects of the shaver controller 116. For example, foot pedal device 138 may be used for on-off control of the motor within the wand 102. Further, foot pedal device 140 may be used to control and/or set rotational mode of the rotating portion of the mechanical resection instrument 104. Alternatively, control of the various operational or performance aspects of the shaver controller 116 may be activated by selectively depressing finger buttons 148 located on the MDU 110 of the wand 102.

Figure 2:
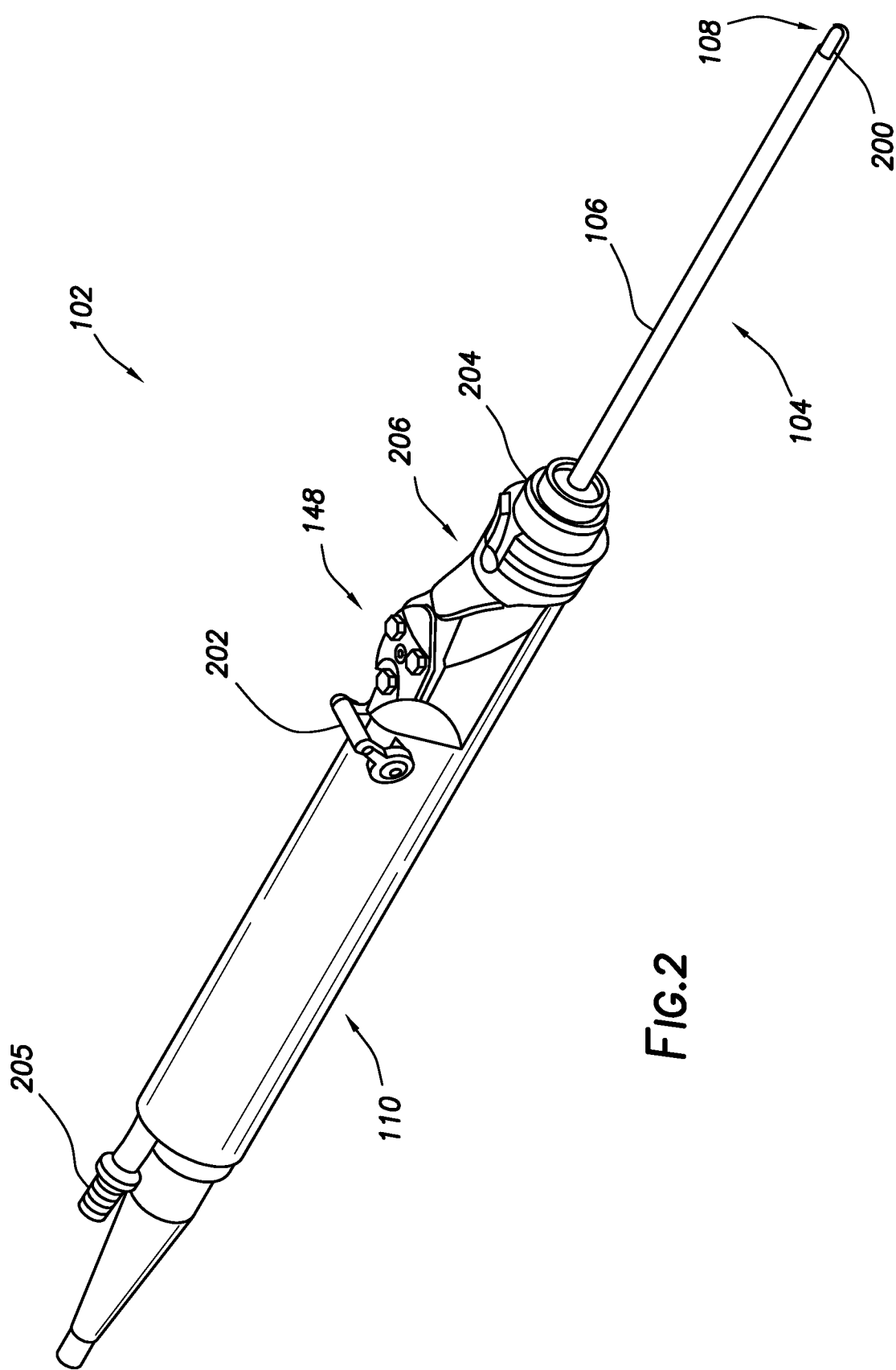
FIG. 2 shows a perspective view of a wand in accordance with at least some embodiments.

FIG. 2 shows a perspective view of a wand 102 in accordance with at least some embodiments. In particular, visible in FIG. 2 is the example MDU 110 as well as the example mechanical resection instrument 104. In the example wand 102 of FIG. 2, the mechanical resection instrument 104 is a blade-type device where the elongate shaft 106 is defined by an outer tube, and telescoped within the outer tube is an inner member (not visible). At the distal end 108 a cutting window 200 is provided through the elongate shaft 106. Though not specifically shown, the inner member in the form of an inner tube is telescoped within the outer tube, and the inner tube has a corresponding window. When the windows in the inner tube and outer tube align, tissue is drawn into the cutting window 200, and the interaction of the cutting surfaces of the outer and inner tubes cuts the tissue. In the case of the mechanical resection instrument being a blade-type device, suction provided by the peristaltic pump 124 draws fluid and resection byproducts through the outer tube; and more particularly, the peristaltic pump draws fluid and resection byproducts through the inside diameter of the inner tube. Other types of mechanical resection instruments may be used, such as burr-type devices where the inner member is a tube having a burr or scraper on a distal end thereof. The scraper or burr is exposed at the distal end 108, and tissue is resected by the scraper or burr grinding or scraping away the tissue. In the case of the mechanical resection instrument being a burr-type device, suction provided by the peristaltic pump 124 draws fluid and resection byproducts through a port in the inner tube proximal to the burr.

Also visible in FIG. 2 are the buttons 148 that the surgeon may use to control various aspects of the operation of the wand 102 (e.g., rotational mode, aggressiveness of aspiration through the wand 102). FIG. 2 further shows that the MDU 110 may implement a suction lever 202. The suction lever 202 is rotationally coupled to an outside surface of the MDU 110. The suction lever 202 is attached to a valve member (not shown in FIG. 2) within the MDU 110. More specifically, the valve member is disposed within a flow channel defined within the MDU 110 (the flow channel fluidly coupled to the hose connector 205). In most cases, the suction lever 202 (and thus the internal valve member) is placed in a fully open position and remains in a fully open position during use, as the modulation of the suction through the wand 102 in various embodiments is controlled by the peristaltic pump 124 (FIG. 1).

The rate at which fluid is drawn through a mechanical resection instrument and the MDU can be based on many factors, including: the specific mechanical resection instrument in use; surgeon preference; the modes of operation of the mechanical resection instrument (e.g., rotation, oscillate); the joint being operated on; the type of surgery; the usage conditions (such as whether the mechanical resection device is interacting with tissue or not); the presence of clog; and other factors. Determining these conditions and setting the appropriate outflow rate is discussed more below.

In many cases, the mechanical resection instrument 104 is a single-use item that is used for a particular surgical procedure, and then disposed of. By contrast, the MDU 110 may be cleaned, sterilized, and reused for multiple surgical procedures. Many different mechanical resection instruments may be coupled to the MDU 110 (and thus coupled to the shaver controller 116 (FIG. 1)). The different mechanical resection instruments include not only the categories of blade-type and burr-type devices, but also variations within each category. For example, there may be many blade-type devices from which a surgeon may choose, such as blade-type devices having varying outside diameters of the elongate shaft 106, varying axial lengths of the elongate shaft 106 (i.e., lengths measured parallel to a longitudinal axis through the inside diameter of the outer tube that defines the elongate shaft 106), and varying aggressiveness of cutting surfaces (e.g., smooth, toothed). As yet another example, there may be many burr-type devices from which a surgeon may choose, such as burr-type devices having varying outside diameters of the elongate shaft 106, varying axial lengths of the elongate shaft, and varying aggressiveness of the grinding surface of the burr (e.g., aggressive grinding surfaces for macro-scale work, and less aggressive grinding surfaces for sculpting work). Regardless of the mechanical resection instrument selected (and, in fact, multiple can be used in any one surgical procedure), each mechanical resection instrument 104 includes a coupler 204 designed and constructed to couple to a distal end 206 of the MDU 110. When the coupler 204 is mechanically coupled to the distal end 206 of the MDU 110, the flow pathway within the mechanical resection instrument 104 is fluidly coupled to the flow channel through the MDU 110, and the rotating portion (e.g., the inner member) of the mechanical resection instrument is mechanically coupled to the motor within the MDU 110.

Figure 3:
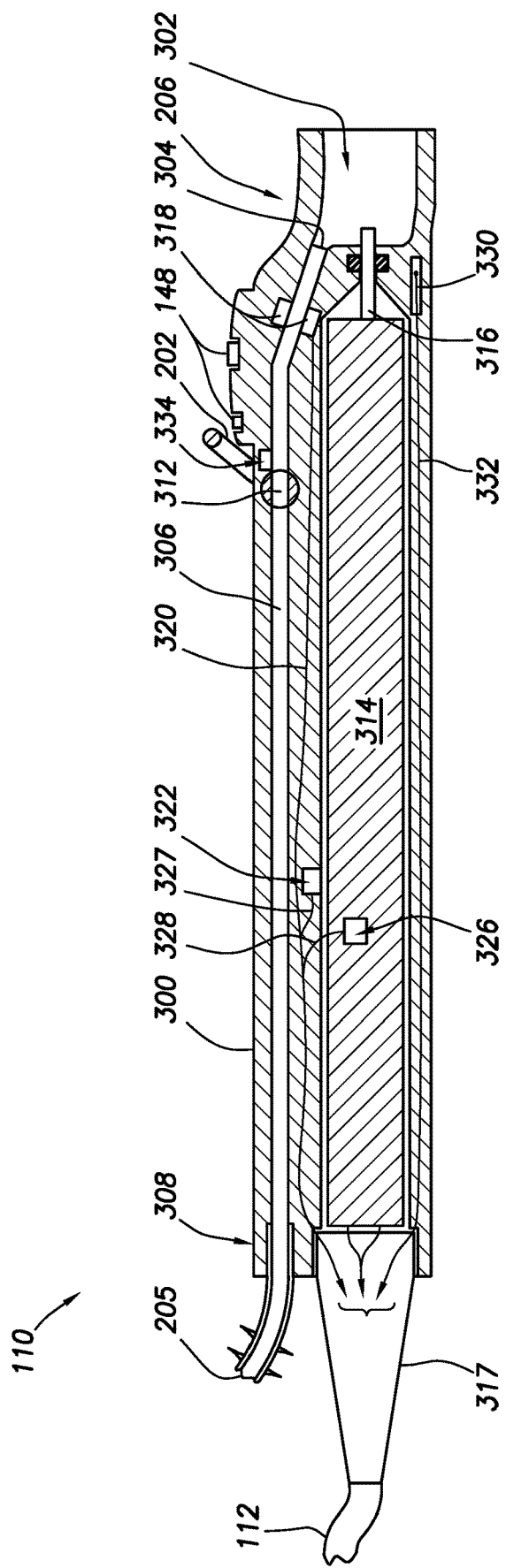
FIG. 3 shows a cross-sectional view of the motor drive unit (MDU) in accordance with at least some embodiments.

FIG. 3 shows a cross-sectional view of the MDU 110 in accordance with at least some embodiments. In particular, the example MDU 110 comprises an outer casing 300 that defines an outside surface where the surgeon grips the MDU 110 during surgical procedures. Exposed on the outside surface of the outer casing 300 are the buttons 148 discussed above. The distal end 206 of the MDU 110 includes a receptacle 302 into which the coupler 204 (FIG. 2) is inserted when the mechanical resection instrument 104 (FIGS. 1 and 2) is mated with the MDU 110. In the example system, the receptacle 302 and coupler 204 are constructed such that the coupler 204 telescopes into the inside diameter of the receptacle 302, but any coupling mechanism may be used (e.g., the coupler telescopes over the distal end 206 of the MDU 110). Within the receptacle 302 is defined an aperture 304 that leads to the flow channel 306 through the MDU 110. In the example MDU 110 of FIG. 3, the flow channel 306 initially transitions upward, and then is straight for the remaining length of the MDU 110. At the proximal end 308 of the MDU 110 resides a hose connector 205 that is fluidly coupled to the flow channel 306. The hose connector 205 enables connection to the flexible tubular member 122 (FIG. 1).

FIG. 3 also shows the suction lever 202 rotationally coupled to the outside surface of the outer casing 300 of the MDU 110. The suction lever 202 is rigidly coupled to an example internal valve member 312 in operational relationship with the flow channel 306. In one rotational orientation of the suction lever 202 and thus valve member 312, and as shown in FIG. 3, the valve member 312 presents no impediment to the flow of the fluids and/or resection byproducts through the flow channel 306. In a second rotational orientation of the suction lever 202 and thus valve member 312 (not shown), the valve member 312 may be oriented such that some impediment to the flow of the fluids and/or resection byproducts through the flow channel 306 is present.

The example MDU 110 further comprises a motor 314 that defines a drive shaft 316. The motor 314 is disposed within the outer casing 300 of the MDU 110, and the drive shaft 316 is exposed within the receptacle 302. When a coupler 204 (not shown) of a mechanical resection instrument 104 is coupled to the MDU 110, the rotating portion of the mechanical resection instrument (e.g., inner tubular member) is mechanically coupled to the drive shaft 316 such that the motor 314 can control rotation of the rotating portion. The motor 314 may take any suitable form, such as a brushless Direct Current (DC) motor, stepper motor, Alternating Current (AC) motor, or even a pneumatic motor. While FIG. 3 shows the drive shaft 316 extending into the receptacle 302 for direct coupling to the rotating portion of the mechanical resection instrument, in other cases various gears may be disposed between the drive shaft 316 and the rotating portion of the mechanical resection instrument to set the relationship between drive shaft 316 rotational speed and rotational speed of the rotating portion of the mechanical resection instrument. Assuming the motor 314 is an electrical motor for purposes of the further disclosure, electrical leads that couple to windings of the motor 314 feed through the connector 317 and into the flexible multi-conductor cable 112.

The motor 314 may operate in several different rotational modes. For example, one rotational mode is a forward rotation mode, where the motor 314 turns the rotating portion of the mechanical resection instrument in a single and continuous rotational direction. The forward rotation mode may be used for engaging specific cutting surfaces of a blade-type device with the tissue, or engaging the teeth of a burr-type device in such a way to provide more aggressive cutting and/or scraping of the tissue. Another example rotational mode may be a reverse rotation mode, where the motor (and thus the rotating portion of the mechanical resection instrument) turns in a direction opposite the forward rotation mode. The reverse rotation mode may be used for engaging different specific cutting surfaces of a blade-type device (e.g., the cutting surface on the opposite side of the cutting window of a blade-type device), or engaging the teeth of a burr-type device in such a way as to provide less aggressive cutting and/or scraping of the tissue (e.g., for tissue smoothing or sculpting functions). Yet still another example rotational mode is an oscillation mode in which the motor (and thus the rotating portion) oscillates back and forth about a particular rotational orientation. For example, for a blade-type device the fixed rotational position may be alignment of the cutting window of the outer tube (i.e., outer window) and the cutting window of an inner member (i.e., inner window). Thus, by rotating in a first direction, a first cutting surface of the outer window engages with a first cutting surface of the inner window. And then by rotating in a second direction opposite the first direction, a second cutting surface of the outer window engages with a second cutting surface on the inner window. Other modes, and sub-modes, are possible. For example, within one of the continuous modes (e.g., forward or reverse), the speed of the rotation may be controlled. For example, in the forward mode the speed may slow when the inner window aligns with the outer window to provide time for the suction or aspiration to draw tissue in, and then the speed increases to provide crisp cutting action as between the cutting surfaces.

In accordance with example embodiments, the MDU 110 further comprises one or more means for sensing use of the MDU. More particularly, in example embodiments the MDU 110 comprises one or more sensors that sense a parameter indicative of resection by a mechanical resection instrument coupled to the MDU 110. In accordance with various embodiments, a parameter indicative of resection is a parameter that directly or indirectly indicates that a distal end of a mechanical resection instrument is being used to resect tissue (including bone). The fact that the motor 314 is turning alone is not necessarily indicative of resection, as the rotating portion can be rotating the cutting, scraping, and/or grinding component of the mechanical resection instrument, but the cutting, scraping, and/or grinding component not be in contact with tissue and thus not performing resection. The means for sensing may take many forms, and in fact several means for sensing may be implemented simultaneously within example MDU 110.

Still referring to FIG. 3, the MDU 110 implements an example means for sensing a parameter indicative of resection in the form of a resection byproducts sensor 318 in operational relationship to the flow channel 306 through the MDU 110. In particular, the example resection byproducts sensor 318 is positioned close to the receptacle 302, and in particular is located between the valve member 312 and the receptacle 302 to be close to the fluid exiting the receptacle 302. The resection byproducts sensor 318 itself may take many forms. One example form is an optical sensor on one side of the flow channel 306, and source of electromagnetic energy (e.g., visible light) on the opposite side of the flow channel 306. The presence of resection byproducts tends to block light crossing the flow channel 306 such that an amount of light received by the optical sensor portion is inversely proportional to the amount of resection byproducts passing the sensor. In other example cases, the source of electromagnetic energy may be tuned to one or more frequencies that are absorbed by blood cells, and thus the amount of electromagnetic energy that reaches the sensor portion is inversely proportional to the amount of blood (a resection byproduct) in the flow channel 306 being aspirated from the surgical site. Other example sensors include pH sensors (which sense change in pH as indicative of resection byproducts, particularly blood), impedance sensors which sense change of electrical impedance (indicative of resection byproducts, including blood), and ultrasonic sensors (which may differentiate resection byproducts and air bubbles based on the amount of ultrasonic signal reflected and/or transmitted). The electrical leads 320 for the example resection byproducts sensor 318 may run within the outer casing 300 at any suitable location, eventually finding their way to the connector 317 and flexible multi-conductor cable 112. The resection byproducts sensor 318 communicatively couples to the shaver controller 116 by way of the leads 320. While the example resection byproducts sensor 318 is shown disposed between the valve member 312 and the receptacle 302, the resection byproducts sensor 318 may be placed at any suitable location within the MDU, such as between the hose connector 205 and the valve member 312. If the shaver controller 116 (FIG. 1) senses a value indicative of the amount of resection byproducts in the flow channel 306 as being above a predetermined threshold, the shaver controller 116 may increase the rate at which fluid is drawn through the mechanical resection instrument and the MDU 110. The increased rate at which fluid is drawn may help clear the visual field for the surgeon, may increase efficiency of the resection, and may reduce the chances of clogging. Once the value indicative of the amount of resection byproducts falls below the predetermined threshold (e.g., during periods of time when the mechanical resection instrument is not being used for resection), the shaver controller 116 may return to the initial outflow rate.

The example MDU 110 may also implement another example means for sensing a parameter indicative of resection in the form of a vibration sensor 322 operationally coupled to the motor 314. In particular, the example vibration sensor 322 is shown positioned in close proximity to the motor 314, and in some cases the vibration sensor 322 is coupled directly to and/or abuts the stator (i.e., stationary outer portion) of the motor 314. The vibration sensor 322 itself may take many forms. One example form is a single axis accelerometer having a sensitivity axis perpendicular to the rotational axis of the drive shaft 316. In other cases, the sensitivity axis may be tangent to a cross-section of the stator of the motor, the cross-section perpendicular to the rotational axis of the drive shaft 316. The tangent orientation may enable sensing not only vibration generally, but specifically vibration associated with varying torque applied to the mechanical resection instrument by the motor during resection, and particularly cutting action by blade-type devices. In other cases, the vibration sensor 322 may be a multi-axis vibration sensor (e.g., three-axis sensor) such that vibration in all three spatial coordinates is measured. The example vibration sensor 322 is coupled to electrical leads 324. The electrical leads 324 for the example vibration sensor 322 may run within the outer casing 300 at any suitable location, eventually finding their way to the connector 317 and flexible multi-conductor cable 112. The vibration sensor 322 thus communicatively couples to the shaver controller 116 by way of the leads 324. Vibration sensed by the vibration sensor 322 may be indicative use of the MDU 110 (and attached mechanical resection instrument) in resection of tissue, including vibration indicative of changes in torque provided by the motor 314. In some cases, the shaver controller 116 may filter (e.g., low-pass filter, band-pass filter) the signal from the vibration sensor 322 to leave only the frequency range(s) of interest. If the shaver controller 116 senses a value indicative of vibration (or torque) of the motor as being above a predetermined threshold, the shaver controller 116 may increase the rate at which fluid is drawn through the mechanical resection instrument and the MDU 110. The increased rate at which fluid is drawn may help clear the visual field for the surgeon, may increase efficiency of the resection, and may reduce the chances of clogging. Once the value indicative of vibration (or torque) falls below the predetermined threshold (e.g., during periods of time when the mechanical resection instrument is not being used for resection), the shaver controller 116 may return to the initial outflow rate.

The example MDU 110 also implements another example means for sensing a parameter indicative of resection in the form of a temperature sensor 326 operationally coupled to the motor 314. In particular, the example temperature sensor 326 may be coupled in close proximity to the motor 314, and in some cases the temperature sensor 326 is coupled directly to and/or abuts the stator of the motor 314. The temperature sensor 326 may take many forms, such as a thermocouple, thermistor, or resistive thermal device (RTD). The example temperature sensor 326 is coupled to electrical leads 328. The electrical leads 328 for the temperature sensor 326 may run within the outer casing 300 at any suitable location, eventually finding their way to the connector 317 and flexible multi-conductor cable 112. The temperature sensor 326 thus communicatively couples to the shaver controller 116 by way of the leads 328. Temperature sensed by the temperature sensor 326 may be indicative use of the MDU 110 (and attached mechanical resection instrument) in actual resection of tissue. If the shaver controller 116 (FIG. 1) senses a value indicative of temperature of the motor as being above a predetermined threshold, the shaver controller 116 may increase the rate at which fluid is drawn through the mechanical resection instrument and the MDU 110. The increased rate at which fluid is drawn may help clear the visual field for the surgeon, may increase efficiency of the resection, and may reduce the chances of clogging. Moreover, and as mentioned above, some MDU devices use fluid flow through the MDU to cool the motor 314, and thus the increased rate at which fluid is drawn may also increase the cooling associated with the motor 314. Once the value indicative of temperature falls below the predetermined threshold (e.g., during periods of time when the mechanical resection instrument is not being used for resection), the shaver controller 116 may return to the initial outflow rate.

Still referring to FIG. 3, the example MDU 110 further comprises a radio frequency identification (RFID) tag reading antenna 330. In some embodiments, and as shown, the antenna 330 is disposed within the outer casing 300. In other cases, and depending on the antenna type (e.g., an antenna created on thin film), the antenna 330 may be coupled to an outside surface of the outer casing 300. Moreover, the example antenna 330 is disposed on the distal end 206 of the MDU, on the side opposite the buttons 148. The antenna 330 is coupled to electrical leads 332. The electrical leads 332 for the antenna 330 may run within the outer casing 300 at any suitable location, eventually finding their way to the connector 317 and flexible multi-conductor cable 112. The antenna 330 thus communicatively couples to the shaver controller 116 (FIG. 1) by way of the leads 332. In accordance with example systems and methods, the shaver controller 116 reads an RFID tag associated with a mechanical resection instrument by way of the antenna 330. The shaver controller 116 may thus identify the mechanical resection instrument by way of the RFID tag to create an identified instrument. The shaver controller 116 may then set various parameters (e.g., an initial outflow rate) based on the identified instrument.

Figure 4:
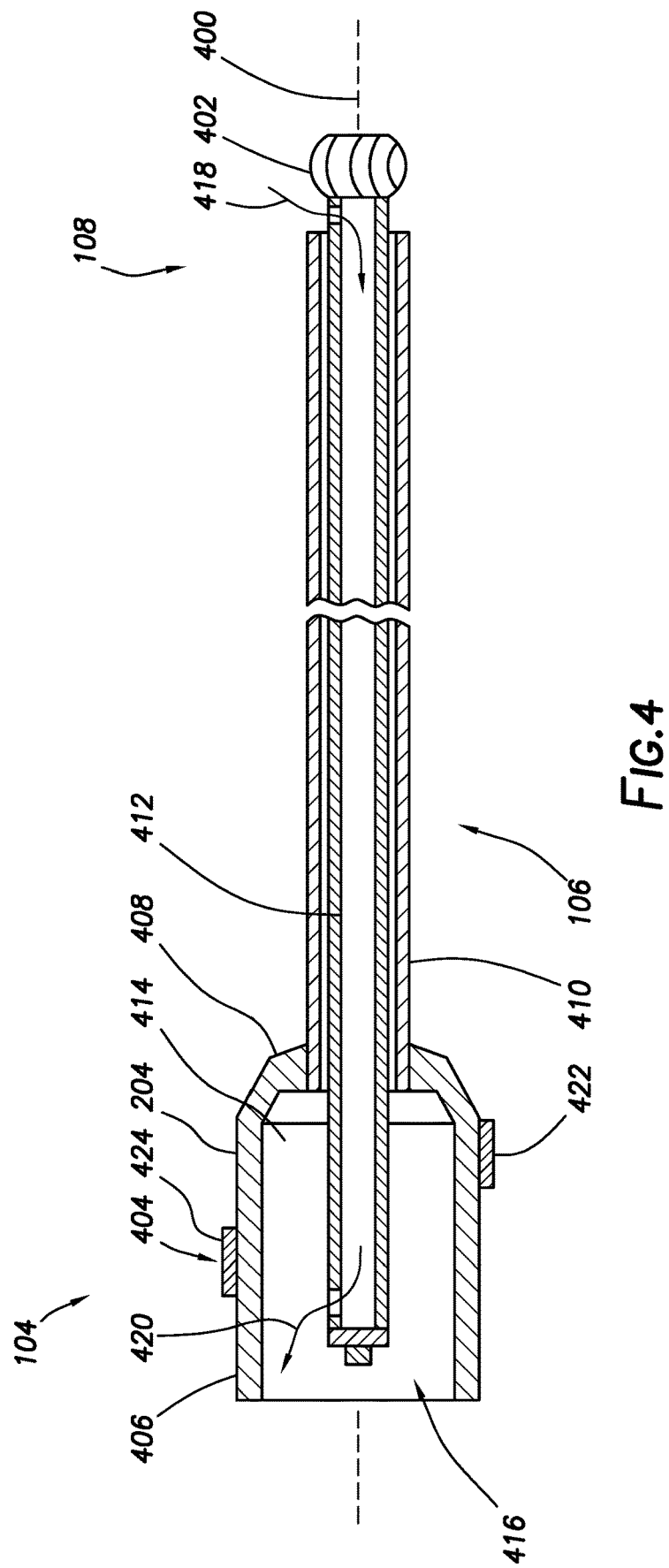
FIG. 4 shows a side elevation, partial cross-sectional, view of a mechanical resection instrument in accordance with at least some embodiments.

FIG. 4 shows a side elevation, partial cross-sectional, view of mechanical resection instrument in accordance with at least some embodiments. In particular, FIG. 4 shows an example mechanical resection instrument 104 in the form of a burr-type device. The cross-sectional view is taken through the longitudinal axis 400; however, the burr 402 is not shown in cross-section. The example mechanical resection instrument 104 comprises the coupler 204 on the proximal end 404. As discussed above, the coupler 204 is designed to mate with the receptacle 302 of the MDU 110 (FIG. 3). The coupler 204 defines a side wall 406 and an end cap 408. The end cap 408 protrudes in the distal direction. The elongate shaft 106 is defined by an outer tube 410 that telescopes within and seals to the end cap 408. FIG. 4 further shows an example inner tube 412 telescoped within the outer tube 410. The proximal end of the inner tube 412 extends into an internal volume 414 of the coupler 204, and the proximal end of the inner tube 412 is configured to couple to the drive shaft 316 of the MDU 110 (FIG. 3). Moreover, in the example case of FIG. 4 the cutting element on the distal end 108 of the inner tube 412 is the burr 402, and the burr 402 is at least partially exposed beyond the distal end of the outer tube 410.

The internal volume 414 defines a slough chamber 416. In use, resection byproducts and fluid may be drawn into the inside diameter of the inner tube 412 at the distal end 108 (as shown by arrow 418) through an aperture or port. The resection byproducts and fluid travel through the inside diameter of the inner tube 412 toward the proximal end 404, and exit one or more apertures at the proximal end of the inner tube 412, thus moving into the slough chamber 416 (as shown by arrow 420). The resection byproducts and/or fluid are then drawn through the aperture 304 (FIG. 3) that leads the flow channel 306 (FIG. 3) of the MDU 110. In use during resection, the drive shaft 316 of the motor 314 (FIG. 3) turns the inner tube 412, and thus the various apertures into which resection byproducts and fluid flow are rotating.

Still referring to FIG. 4, the example mechanical resection instrument 104 further comprises an RFID tag 422. In some cases, and as shown, the RFID tag 422 is coupled to an outside surface (e.g., the outside diameter) of the coupler 204 at a location that does not interfere with telescoping the coupler 204 into the receptacle 302 of the MDU 110. Further as shown, the example RFID tag 422 may be placed on the coupler 204 on the side opposite an alignment pin 424. In other cases, the RFID tag 422 may be placed at any suitable location, such as inside the slough chamber 416, or embedded within the material of the coupler 204. In some cases, the location of the RFID tag is close to the location of the antenna 330 (FIG. 3) to enable reading of the RFID tag 422. The RFID tag 422 itself may take any suitable form, such as an active tag, a passive tag, a tag that affirmatively transmits electromagnetic waves, or a tag that conveys information by controlling reflections from an antenna (not specifically shown) of the RFID tag 422. As discussed in relation to the antenna 330 (FIG. 3), the shaver controller 116 (FIG. 1) is configured to identify the mechanical resection instrument 104 coupled to the MDU 110 by way of the RFID tag 422 and antenna 330, which creates the identified instrument. Moreover, the shaver controller 116 may be configured to set an outflow rate based on the identified instrument and other information, such as an indication of rotational mode.

Figure 5:
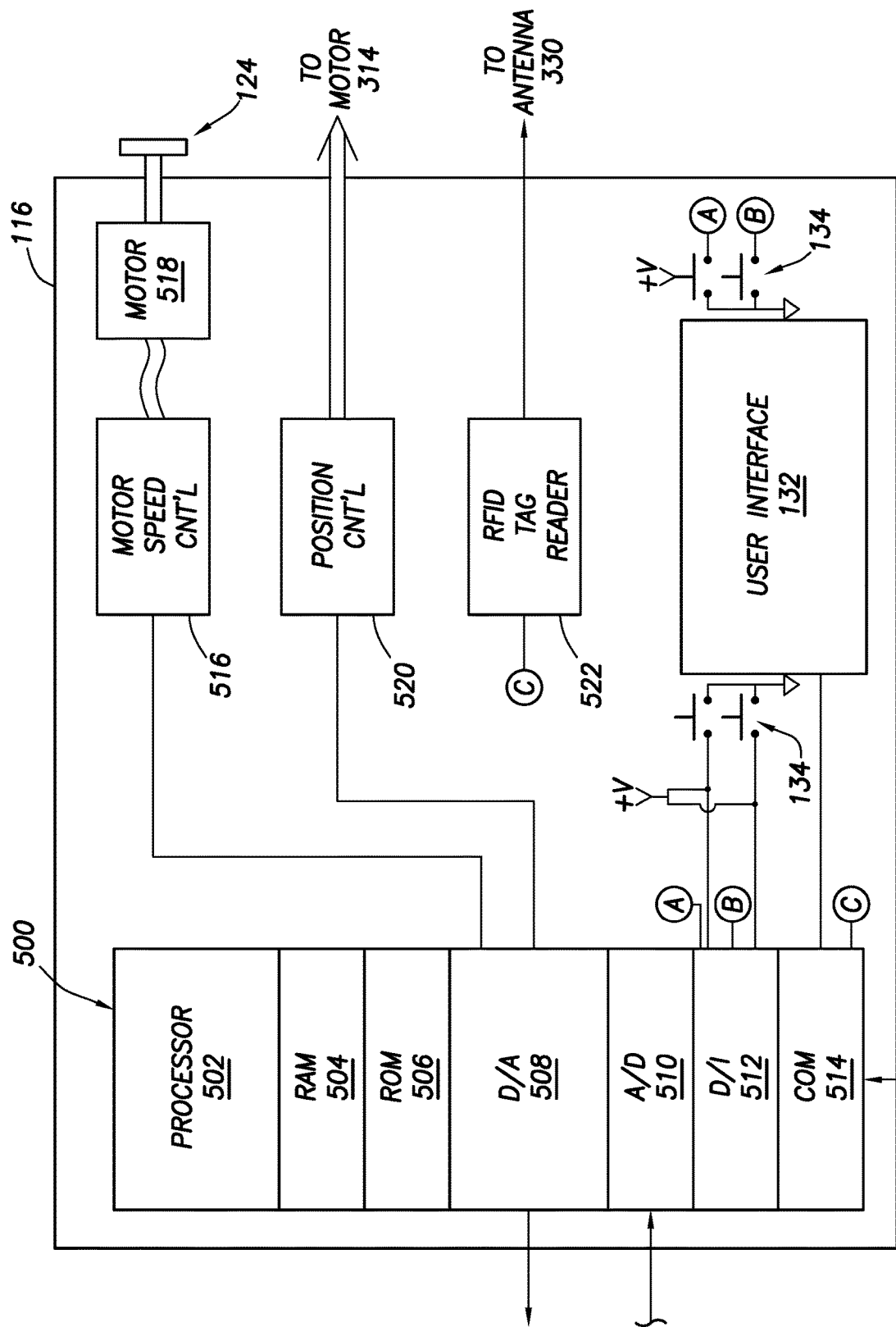
FIG. 5 shows, in block diagram form, an example shaver controller in accordance with at least some embodiments.

FIG. 5 shows, in block diagram form, an example shaver controller 116 in accordance with at least some embodiments. In particular, the example shaver controller 116 has a control system 500 coupled to various internal and external components. In the example system of FIG. 5, the control system 500 takes the form of a microcontroller having processor 502 electrically coupled to random access memory (RAM) 504, read-only memory (ROM) 506, digital-to-analog (D/A) outputs 508, analog-to-digital (A/D) inputs 510, digital inputs (D/I) 512, as well as communication logic (COM) 514 sections. Though control system 500 is shown in the form of a microcontroller, in other cases individual components (i.e., an individual processor, RAM, ROM, etc.) may be combined to implement the functionality, or other devices such as FGPAs, ASICs, PLCs, and discrete components may be used. The example RAM 504 may be the working memory for the processor 502. ROM 506 may store programs and data in a non-volatile fashion, and the processor 502 may copy the programs and data from the ROM 506 to RAM 504 during execution of the programs. The digital-to-analog outputs 508 may be used to provide analog signals to other devices within the shaver controller 116, such as the pump motor speed controller 516 (discussed more below), or to external devices. The analog-to-digital inputs 510 may provide the control system 500 the ability to read analog signals, such as signals from the means for sensing use of the MDU (e.g., from FIG. 3: resection byproducts sensor 318; vibration sensor 322; and temperature sensor 326). The digital inputs 512 may be used to receive information into the control system 500, such as information from the foot pedal devices 138/140, buttons 134 of the shaver controller 116, or buttons 148 on the MDU 110. Finally, the communication logic 514 may be used for packet-based communications with internal or external devices (e.g., user interface 132, or as an alternate means to communicate with the pump motor speed controller 516 and position controller 520).

Regardless of the mechanism by which the shaver controller 116 receives information, the control system 500 may implement various modes of operation related to outflow rates through the mechanical resection instrument, rotational modes of the rotating portion of the mechanical resection instrument, and changes in outflow responsive to indications of use of the mechanical resection instrument to resect tissue. With respect to suction or outflow control, the example shaver controller 116 implements a pump motor speed controller 516 coupled to a motor 518, where the peristaltic pump 124 is turned by the motor 518. The motor 518 may take any suitable form. For example, the motor 518 may be a DC electric motor, and thus the pump motor speed controller 516 provides a DC voltage to the electric motor which controls the speed of the output shaft. In other cases, the motor 518 may be an AC electric motor, and thus the motor speed controller 516 provides an AC voltage at varying voltage and frequency which controls the speed of the output shaft. In yet still other cases, the motor 518 may be a pneumatic motor, and thus the pump motor speed controller 516 provides air at varying pressures, where the pressure controls the speed of the output shaft. Thus, regardless of the type of motor 518 implemented, the pump motor speed controller 516 controls the speed of the motor responsive to commands provided from the control system 500. While in the example system the command to the pump motor speed controller 516 is shown to be an analog signal, in other cases the motor speed controller 516 may receive commands in packet-based messages (e.g., through the communication logic 514). Finally, while the motor 518 is shown to directly couple to the peristaltic pump 124, in other cases various gears and/or belts may be used to transfer the rotational motion of the shaft of the motor 518 to peristaltic pump 124. While FIG. 5 is based on having a rotary peristaltic pump, one having ordinary skill and with the benefit of this disclosure could modify the system to be used with other types of outflow pumps, such as linear peristaltic pump or centrifugal pumps combined with flow measurement devices (as the flow rate through a centrifugal pumps is not as directly related to speed as is a positive displacement pump (such as a peristaltic pump)).

Before proceeding, it is noted that the embodiments of FIG. 5 show the peristaltic pump 124 as an internal or integral device with the shaver controller 116 (e.g., within the same enclosure); however, in other cases the peristaltic pump 124 may be an external component to the shaver controller 116. Moreover, while only one connected set of pump motor speed controller, motor, and peristaltic pump is shown in FIG. 5, a shaver controller may implement two or more (e.g., also including an inflow peristaltic pump).

Still referring to FIG. 5, the example shaver controller 116 further implements a second motor controller in the form of a position controller 520. The position controller 520 couples to the motor 314 (FIG. 3) within the MDU 110, where the rotating portion of the mechanical resection instrument is turned by the motor 314. As discussed above, the motor 314 within the MDU 110 may take any suitable form, including AC, DC, stepper, and pneumatic. Regardless of the type of motor 314 implemented within the MDU 110, the position controller 520 controls the speed and/or position of the rotor or drive shaft of the motor 314 responsive to commands provided from the control system 500. While in the example system the command to the position controller 520 is shown to be an analog signal, in other cases the position controller 520 may receive commands in the form of packet-based messages (e.g., through the communication logic 514).

The example shaver controller 116 of FIG. 5 further implements an RFID tag reader 522. The RFID tag reader 522 electrically couples to the antenna 330 (FIG. 3) within the MDU 110. The example RFID tag reader 522 couples to the control system 500 by way of the communication logic 514, but any suitable communicative coupling may be used. As alluded to above, in example systems the shaver controller 116 is configured to identify the mechanical resection instrument coupled to the MDU 110 by way of the RFID tag 422 (FIG. 4) and RFID tag reader 522. Identifying the mechanical resection instrument creates an identified instrument, and the identification may directly or indirectly inform the control system 500 at least of an outflow rate to use for the surgical procedure.

Thus, in example embodiments the control system 500 comprises RAM 504 and ROM 506 (and possibly other non-transitory storage mediums) that store instructions that implement the outflow control strategies discussed below. Example instructions, when executed by the processor, may cause the shaver controller to: receive an indication of a rotational mode of a rotating portion of the mechanical resection instrument coupled to the motor of the MDU; control rotation of the rotating portion of the mechanical resection instrument by controlling the motor of the MDU, the controlling in conformance with the indication of the rotational mode; set a first outflow rate through the MDU and mechanical resection instrument based on the indication of the rotational mode; draw fluid through the mechanical resection instrument at the first outflow rate during the surgical procedure, the drawing by way of the peristaltic pump; sense a parameter indicative of resection by the mechanical resection instrument; and change a rate at which fluid is drawn through the mechanical resection instrument, the changing relative to the first outflow rate, and the changing responsive to the parameter indicative of resection.

In yet still other cases, the control may be, in whole or in part, implemented in an FPGA, PLD, PLC, ASIC or even in discrete components (e.g., capacitors, resistors, operational amplifiers), such that the discrete components operate to control the speed of the peristaltic pump and rotation of the motor 314 within the MDU 110. In these situations, the modes of operation may be implemented by electrically controlled switches selectively switching in and out various circuit components (e.g., capacitors, resistors), or in other cases the shaver controller 116 may implement multiple discrete proportional-integral-differential (PID) controllers hard wired with particular but different PID parameters, and thus changing modes may involve changing between the PID controllers themselves rather than just changing parameters of a single PID controller.

Figure 6:
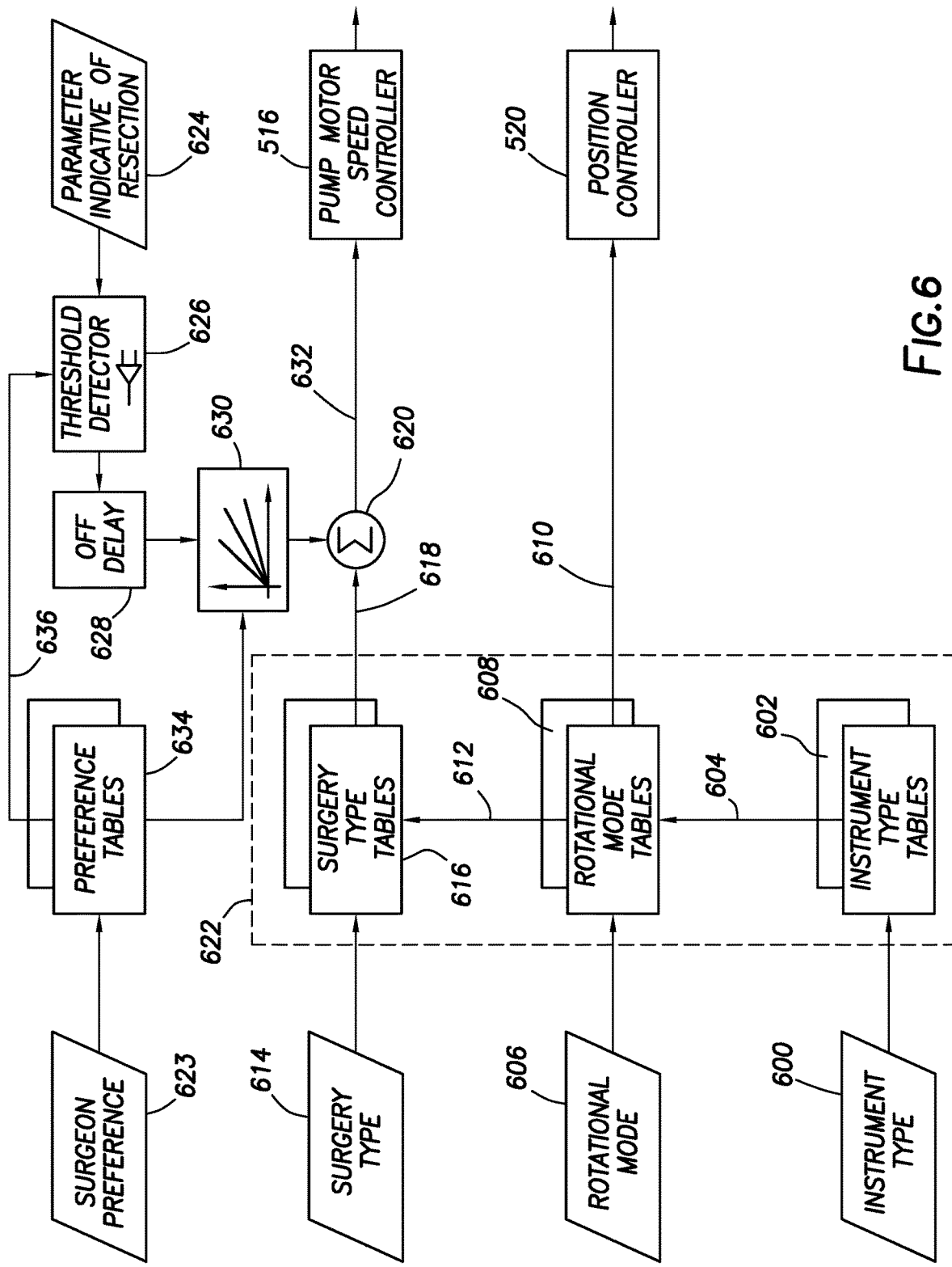
FIG. 6 shows, in block diagram form, process control implemented in a shaver controller in accordance with at least some embodiments.

FIG. 6 shows, in block diagram form, process control implemented in a shaver controller 116 in accordance with at least some embodiments. In particular, the process control illustrated in FIG. 6 may be implemented by the control system 500 and related components shown and discussed with respect to FIG. 5. The process control of FIG. 6 will be discussed approximately in the order that the surgeon would approach setting up and utilizing the shaver controller 116 for a surgical procedure.

Referring simultaneously to FIGS. 5 and 6, in example embodiments a mechanical resection instrument 104 is coupled to the MDU 110. In the example system, the RFID tag reader 522 reads the RFID tag 422 (FIG. 4) to identify the mechanical resection instrument 104, and the reading creates an identified instrument or instrument type 600. While example embodiments utilize the RFID tag 422, other systems and methods may be used to provide the instrument type 600. For example, detection may be alternatively accomplished by magnets in the coupler of the mechanical resection instrument (and reed switches in the MDU), reading one-dimensional or two-dimensional barcodes printed on the instrument, or the surgeon may provide the instrument type directly to the shaver controller 116 (e.g., by way of the interface device 132 and buttons 134). In some cases, the instrument type 600 is a broad category, such as the instrument type being a blade-type device, or a burr-type device. In other cases, particularly cases using RFID tags, the specific instrument may be identified, including information such as manufacturer, model, internal dimensions (e.g., tube sizes and lengths), and features of the cutting/scraping elements (e.g., straight cutting elements, toothed cutting elements, or burr-type).

Based on the instrument type 600, the example shaver controller 116 may create or select an initial set of outflow rates by reference to the instrument type tables 602. In some cases, the instrument type tables 602 may reside in the shaver controller 116 prior to the shaver controller 116 being coupled to the mechanical resection instrument 104. In other cases, the instrument type tables 602 may be stored on the RFID tag 422 and transferred to the shaver controller 116 by reading the RFID tag 422 by way of the RFID tag reader 522. Nevertheless, based on the instrument type 600 an initial set of outflow rates is determined. For example, the following table may be stored within the shaver controller 116 or may be provided to the shaver controller 116:

TABLE 1

| Group | Flow Rate | | |
| --- | --- | --- | --- |
| | Base Flow Rate Rotation | Base Flow Rate Oscillate | Base Flow Rate Idle |
| 1 | 100 | 75 | 50 |
| 2 | 150 | 100 | 75 |
| 3 | 200 | 150 | 75 |

Based on the instrument type 600, the shaver controller 116 determines an initial set of outflow rates. As an example, if the instrument type 600 identifies the mechanical resection instrument 104 as a Group 2 device, the initial set of outflow rates is the set on the horizontal row of the table associated with Group 2, and the initial set of outflow rates is passed to the next step in the analysis, as shown by arrow 604.

Next, the surgeon may select a rotational mode of the mechanical resection instrument. For example, the surgeon may interact with a foot pedal of the foot pedal device 138 (FIG. 1), interface with the user interface 132 and buttons 134 (FIG. 1), or interact with the buttons 148 on the MDU 110 (FIG. 1). Thus, the surgeon selects a rotational mode, such as forward rotation, reverse rotation, or oscillation. The selection creates rotational mode 606, which is passed to the position controller 520 coupled to the motor 314 (FIG. 3) of the MDU 110, as illustrated by arrow 610. Moreover, based on the rotational mode 606 the example shaver controller 116 may also select an outflow rate by reference to the rotational mode tables 608. As before, in some cases the rotational mode tables 608 may reside in the shaver controller 116 prior to the shaver controller 116 being coupled to the mechanical resection instrument 104. In other cases, the rotational mode tables 608 may be stored on the RFID tag 422 and transferred to the shaver controller 116 by reading the RFID tag 422 by way of the RFID tag reader 522. Nevertheless, based on the rotational mode 606 an initial outflow rate is determined. For example, and referring briefly to Table 1 above, if the instrument type 600 is a Group 2 instrument and the rotational mode is forward rotation, the shaver controller 116 may select an initial outflow rate as 150.

In some cases, the initial outflow rate indicated based on the rotational mode 606 and instrument type 600 becomes the outflow rate implemented by the shaver controller 116 by setting the pump motor speed controller 516 to a particular speed (with pump motor speed directly related to outflow rate). However, in other cases the initial outflow rate information is passed (as illustrated by arrow 612) to a further determination regarding surgery type. That is, the type of surgery may dictate more outflow or less outflow. Thus, in example systems the surgeon may select a surgery type within which the mechanical resection instrument will be used. For example, the surgeon may interact with a foot pedal of the foot pedal device 138 (FIG. 1), interface with the user interface 132 and buttons 134 (FIG. 1), or interact with the buttons 148 on the MDU 110 (FIG. 1). Thus, the surgeon selects a surgery type (e.g. shoulder surgery, knee surgery, tonsillectomy). The selection creates a surgery type 614, and based on the surgery type 614 the example shaver controller 116 may select an outflow rate by reference to the surgery type tables 616. As before, in some cases the surgery type tables 616 may reside in the shaver controller 116 prior to the shaver controller 116 being coupled to the mechanical resection instrument 104. In other cases, the surgery type tables 616 may be stored on the RFID tag 422 and transferred to the shaver controller 116 by reading the RFID tag 422 by way of the RFID tag reader 522. Nevertheless, based on the surgery type 614 (and ignoring for the moment the summation block 620), an initial outflow rate is modified to become the selected outflow rate 618 which is ultimately passed to the pump motor speed controller 516.

The description of operation of the shaver controller 116 to this point, in reference to FIG. 6, has assumed three separate determinations to arrive at the selected outflow rate 618. However, one of ordinary skill in the art with the benefit of this disclosure will understand that the information relating instrument type 600, rotational mode 606, and surgery type 614 to a selected outflow rate 618 could be stored in a single multidimensional table 622, such that the shaver controller 116 reads or determines all three input variables (e.g., instrument type, rotational mode, and surgery type), and the multidimensional table 622 indicates directly the selected outflow rate 618. As before, the multidimensional table 622 may reside in the shaver controller 116 prior to the shaver controller 116 being coupled to the mechanical resection instrument 104. In other cases, the multidimensional table 622 may be stored on the RFID tag 422 and transferred to the shaver controller 116 by reading the RFID tag 422 by way of the RFID tag reader 522.

Still referring to FIGS. 5 and 6. Each surgeon may have preferences regarding how responsive the shaver controller 116 is to changing operational conditions during a surgical procedure using the mechanical resection instrument 104.

For example, some surgeons may like an aggressive approach to outflow control, and others may like a less aggressive approach to outflow control. Thus, in example systems the surgeon may select a surgeon preference for aggressiveness of outflow control. For example, the surgeon may interact with a foot pedal of the foot pedal device 138 (FIG. 1), interface with the user interface 132 and buttons 134 (FIG. 1), or interact with the buttons 148 on the MDU 110 (FIG. 1). Thus, the surgeon makes a selection and creates a surgeon preference 623 (e.g., low aggressiveness, medium aggressiveness, high aggressiveness). Based on the surgeon preference 623 the example shaver controller 116 may implement different levels of aggressiveness of outflow control. Before discussing further the different levels of aggressiveness of outflow control, the discussion turns to how the example shaver controller 116 reacts to parameters indicative of resection by the mechanical resection instrument 104.

As discussed above, the example MDU 110 implements one or more sensors for sensing a parameter indicative of resection. For example, the MDU 110 may implement the resection byproducts sensor 318, the vibration sensor 322, and/or the temperature sensor 326. Any one or combination of values sensed by the example sensors may provide an indication that the mechanical resection instrument 104 is in use resecting tissue (including bone), as opposed to the mechanical resection instrument 104 having its distal end within the surgical field, but not actually cutting, scraping, and/or grinding tissue. The shaver controller 116, particularly the control system 500, may read the one or more sensors and sense a parameter indicative of resection 624. During periods of time when the parameter indicative of resection 624 indeed indicates resection is taking place, the shaver controller 116 changes the rate at which fluid is drawn through the mechanical resection instrument 104, the changing relative to the selected outflow rate 618. More particularly, the shaver controller 116 increases the rate at which fluid is drawn through the mechanical resection instrument 104 to be above the selected outflow rate 618 when the parameter indicative of resection 624 is above a predetermined threshold, all while maintaining the rotation of the rotating portion of the mechanical resection instrument 104 in accordance with the rotational mode 606.

Referring again to FIG. 6, the parameter indicative of resection 624 is thus applied to an input of a threshold detector 626. The threshold detector 626 makes the determination as to whether the parameter indicative of resection 624 is above the predetermined threshold, which threshold can be a hard-coded threshold (e.g., threshold for vibration, temperature, and/or presence of resection byproducts), or the threshold can be provided, such as based on surgeon preferences 623 (discussed more below). The output signal of the threshold detector 626 is applied to an off delay block 628 and (skipping for now the selected aggressiveness curves 630) then applied to the summation block 620. Thus, when the threshold detector 626 determines the parameter indicative of resection 624 is above the predetermined threshold, the final outflow rate 632 provided to the pump motor speed controller 516 is increased above the selected outflow rate 618. In further example embodiments, the threshold detector 626 may also implement a time element. That is, the output of the threshold detector 626 may not become asserted until the parameter indicative of resection 624 is above the predetermined threshold for a predetermined period of time.

In some cases, the output signal of the threshold detector 626 is a Boolean value that indicates, based on its asserted or non-asserted state, that resection is or is not taking place, respectively. In other cases, the output signal of the threshold detector may be a value that not only indicates that resection is or is not taking place, but also the magnitude of the value may indicate how aggressively the mechanical resection device 104 is being used. Thus, during times when resection is not taking place (i.e., the parameter indicative of resection 624 is below the predetermined threshold) the output signal of the threshold detector 626 may output a zero. During times when resection is taking place (i.e., the parameter indicative of resection 624 is above the predetermined threshold), the output signal of the threshold detector 626 may be a value whose magnitude is added to the selected outflow rate 618 to arrive at the final outflow rate 632 applied to the pump motor speed controller 516.

The optional off delay block 628 has an input coupled to the threshold detector 626, and (again skipping for now the selected aggressiveness curve 630) an output coupled to the summation block 620. As the name implies, the off delay block 628 passes the output signal (Boolean or otherwise) immediately to the summation block 620 when the value from the threshold detector 626 becomes asserted or non-zero, but the off delay block 628 continues to provide (for a predetermined amount of time) the value to the summation block 620 in spite of the fact that the output signal from the threshold detector 626 has changed to indicate that resection is not taking place (e.g., becomes once again non-asserted, or drops to zero). Thus, the off delay block 628 may continue to drive increased outflow rate for a period of time to ensure that resection byproducts are moved fully through the MDU 110 and flexible tubular member 122 prior to reducing outflow back to the selected outflow rate 618. Thus, whether the off delay block 628 is implemented or not, once the parameter indicative of resection 624 falls below the predetermined threshold, the increased outflow is eventually ceased and the selected outflow rate 618 is passed through the summation block 620 to become the final outflow rate 632.

The example operation shown by FIG. 6 groups values read from the various sensors in the MDU 110 to be the parameter indicative of resection 624 to present all the potential parameters in bulk. However, in example systems implementing multiple sensors to sense parameters indicative of resections, each sensor may have a corresponding threshold detector, off delay block, aggressiveness curves, and input signal to the summation block 620, such that any sensor alone can drive an increased outflow rate, and multiple sensors can drive increased outflow rate in increments based on how many of the sensors sense parameters indicative of resections. That is, a first sensor (e.g., vibration) may sense a value indicative of resection and drive a first incremental increase in outflow rate. And a second sensor (e.g., resection byproducts sensor) may likewise sense a parameter indicative of resection and drive a second incremental increase in outflow rate summed with the first incremental increase in outflow rate to create the final outflow rate 632, and so on. In alternative embodiments, any one of the parameters indicative of resection, when asserted, may result in a predetermined increase in outflow, and the predetermined increase may remain so long as any one of the parameters indicative of resection remain asserted (with or without off delay). Stated otherwise, the output from the respective threshold detectors may be coupled to respective inputs of a functional OR block, and the output of the functional OR block may be coupled to the off delay block 628 and/or the summation block 620. Or the output from the respective off delay blocks (if each sensor has its own dedicated off delay block (i.e., different off delays implemented for parameter associated with teach sensor), may be coupled to respective inputs of a functional OR block, and the output of the functional OR block may be coupled to summation block 620.

Still referring to FIG. 6, and returning now to the idea of surgeon preference 623. As noted above, different surgeons may prefer different levels of aggressiveness as it relates to outflow control during surgical procedures utilizing mechanical resection instruments. In example embodiments, the surgeon preference may be implemented in the portion of the control loop that uses the parameters indicative of resection 624. More particularly, the example shaver controller 116 applies the surgeon preference 623 to preference tables 634. The preference tables 634 may contain information related to various parameters within the process control illustrated by the block diagram of FIG. 6. For example, the surgeon preference 623 may indicate one of three possible aggressiveness modes; low aggressiveness, medium aggressiveness, and high aggressiveness. For purposes of discussion, consider first that the surgeon chooses the low aggressiveness mode. From the preference tables 634, the low aggressiveness state may provide a set point to the threshold detector 626 (as illustrated by arrow 636) that is relatively high. That is, the set point for the threshold detector 626 in the low aggressiveness mode may be relatively high, meaning that the shaver controller 116 does not increase outflow until the parameter indicative of resection 624 is evidencing high resection usage. In the example low aggressiveness mode, less aggressive resection may not result in increases in outflow rate.

In addition to, or in place of, changing the set point provided to the threshold detector 626, the preference tables 634 may also implement a selective aggressiveness curve 630, the selected aggressiveness curve 630 disposed between the example off delay block 628 and the summation block 620. The selected aggressiveness curve 630 may control the magnitude of the increase in outflow rate provided when the parameter indicative of resection 624 indeed indicates resection is taking place. For example, if the output signal of the off delay block 628 is a Boolean signal, when the Boolean signal is asserted the selective aggressiveness curve 630 may provide a numerical value to the summation block 620 indicating an amount to increase the outflow rate, and likewise when the Boolean signal is not asserted the selective aggressiveness curve 630 may provide a zero value to the summation block 620. If the output signal of the off delay block 628 is a numerical value, when the numerical value is non-zero the selective aggressiveness curve 630 may control a gain applied to the numerical value before being applied to the summation block 620. Consider again, for purposes of explanation, that the surgeon preference 623 is the low aggressiveness mode. In the example low aggressiveness mode, the selected aggressiveness curve may be a flat line that provides a gain of one to the value (i.e., no change to the value) passed to the summation block 620.

Now consider that the surgeon selects the high aggressiveness mode. From the preference tables 634, the high aggressiveness mode may provide a set point to the threshold detector 626 (as illustrated by arrow 636) that is relatively low. That is, the set point for the threshold detector 626 in the high aggressiveness mode may be relatively low, meaning that the shaver controller 116 increases outflow even for relatively low resection usage. In the example high aggressiveness mode, even relatively low aggressive resection results in increases in outflow rate. With respect to the selected aggressiveness curve 630 and the high aggressiveness mode, in the situation where the off delay block 628 passes a Boolean signal, the selected aggressiveness curve 630 may apply a higher value to the summation block 620 (i.e., higher than in the low aggressiveness mode) when the Boolean signal is asserted. In the situation where the off delay block 628 passes a numerical value, the selected aggressiveness curve 630 may applying a higher gain (i.e., a gain greater than one, and thus greater than the applied in the low aggressiveness mode) when the off delay block 620 is passing non-zero value. Thus, surgeon preferences can be accounted for in the example resection system 100.

The discussion to the point has assumed that once set, the various parameters remain unchanged. However, during any particular surgical procedure the surgeon may change various parameters, and the system automatically propagates a new selected outflow rate 618 indicated by the change. For example, the surgeon may change oscillation mode at any time (e.g., from forward mode to oscillate mode from Table 1 above, or to idle mode from Table 1 above (for example, by releasing a foot pedal 138/140 (FIG. 1))). When such a change is made, the multidimensional table 622 (or its individual components) may automatically modify the selected outflow rate 618 provided to the summation block 620. Likewise, the surgeon may at any time change the aggressiveness, resulting in a change to the set point provided to the threshold detector 626 and/or the gain implemented by the selected aggressiveness curve 630.

Returning briefly to FIG. 3. As discussed and shown, the example MDU 110 comprises a suction lever 202 coupled to an internal valve member 312. Inasmuch as the outflow rate is controlled by the shaver controller 116, in most operational situations the suction lever 202 (and thus the internal valve member 312) is placed in and remains in a fully open position. However, some surgeons may habitually use the suction lever 202, and more particular some surgeons may tend to push the suction lever 202 toward a more open position to indicate a desire for increased outflow through the mechanical resection instrument sometimes referred to as lavage mode. In accordance with example embodiments, the MDU 110 comprises an internal or external switch (such as switch 334, internally disposed) in operational relationship with the suction lever 202 (and as shown in operational relationship to the internal valve member 312). The suction lever 202 (and internal valve member 312) has a lavage rotational position in which the internal valve member 312 presents no or minimal impediment to the flow of the fluids and/or resection byproducts through the flow channel 306 and example switch 334 is activated. The shaver controller 116 is communicatively coupled to the example switch 334, and the shaver controller 116 is further configured to increase at a rate at which the fluid is drawn through the mechanical resection instrument above the first outflow rate during periods of time when the suction lever 202 is in the lavage rotational position. The switch used to sense the lavage rotational position may be placed at any suitable location (e.g., one of the buttons 148 may be positioned to interact directly with the suction lever in the lavage rotational position).

Figure 7:
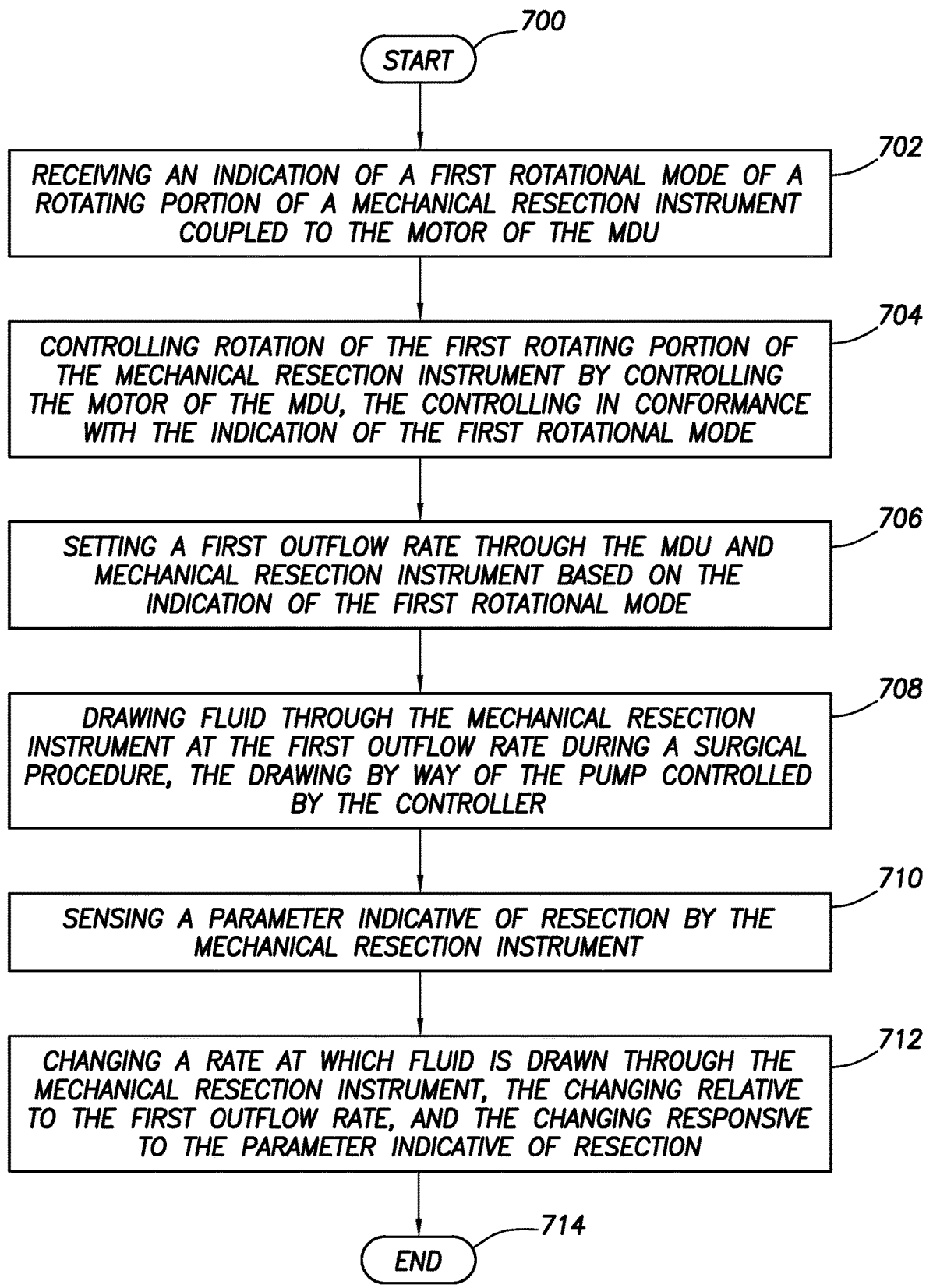
FIG. 7 shows a method in accordance with at least some embodiments.

FIG. 7 shows a method in accordance with at least some embodiments. In particular, the method starts (block 700) and comprises: receiving an indication of a first rotational mode of a rotating portion of a mechanical resection instrument coupled to the motor of the MDU (block 702); controlling rotation of the first rotating portion of the mechanical resection instrument by controlling the motor of the MDU, the controlling in conformance with the indication of the first rotational mode (block 704); setting a first outflow rate through the MDU and mechanical resection instrument based on the indication of the first rotational mode (block 706); drawing fluid through the mechanical resection instrument at the first outflow rate during a surgical procedure, the drawing by way of the pump controlled by the controller (block 708); sensing a parameter indicative of resection by the mechanical resection instrument (block 710); and changing a rate at which fluid is drawn through the mechanical resection instrument, the changing relative to the first outflow rate, and the changing responsive to the parameter indicative of resection (block 712). Thereafter the method ends (block 714).

The above discussion is meant to be illustrative of the principles and various embodiments of the present invention. Numerous variations and modifications will become apparent to those skilled in the art once the above disclosure is fully appreciated. For example, FIG. 6 could be implemented in hardware, software, or combinations thereof. Referring to a signal as a value thus includes not only a software connection passing a value (e.g., a multi-bit value), but also includes passing an electrical signal that has a parameter indicative of the value (e.g., voltage, current, frequency, or phase). It is intended that the following claims be interpreted to embrace all such variations and modifications.

What is claimed is:

1. A system comprising:
    a motor drive unit (MDU) comprising:
        a motor with a drive shaft, the motor disposed within the MDU;
        a flow channel through the MDU; and
        a means for sensing use of the MDU, the means for sensing disposed within the MDU;
    a mechanical resection instrument coupled to the MDU, the mechanical resection instrument comprising:
        a coupler configured to couple to a distal end of the MDU;
        an outer tube mechanically coupled to the coupler;
        an inner member telescoped within the outer tube, the inner member coupled to the drive shaft;
        a flow pathway defined within the outer tube from a distal end of the outer tube to the flow channel of the MDU;
    a fluid pump fluidly coupled to the flow channel within the MDU and the flow pathway within the outer tube;
    a controller electrically coupled to the motor and operationally coupled to the fluid pump, the controller configured to:
        receive an indication of a first rotational mode of the inner member of the mechanical resection instrument;
        control rotation of the inner member by control of the motor of the MDU, the control of the motor in conformance with the indication of the first rotational mode;
        set a first outflow rate through the MDU and mechanical resection instrument based on the indication of the first rotational mode;
        command the fluid pump to draw fluid through the mechanical resection instrument at the first outflow rate;
        sense a parameter indicative of resection by the mechanical resection instrument;
        increase a rate at which fluid is drawn through the mechanical resection instrument above the first outflow rate responsive to the parameter;
        receive an indication of a second rotational mode of the inner member of the mechanical resection instrument, the second rotational mode different than the first rotational mode;
        control rotation of the inner member of the mechanical resection instrument by control of the motor of the MDU, the control in conformance with the indication of the second rotational mode;
        set a second outflow rate through the MDU and mechanical resection instrument based on the indication of the second rotational mode; and
        command the fluid pump to draw fluid through the mechanical resection instrument at the second outflow rate.

2. The system of claim 1 wherein the second rotational mode is at least one selected from a group consisting of: forward rotation; reverse rotation; and oscillation back and forth about a particular rotational orientation.

3. The system of claim 1 wherein when the controller senses the parameter indicative of resection, the controller is further configured to sense that a value indicative of torque supplied by the motor is above a predetermined threshold.

4. The system of claim 3 wherein the controller is further configured to return to the first outflow rate if the value indicative of torque falls below the predetermined threshold.

5. The system of claim 1:
    wherein the MDU further comprises a temperature sensor within the MDU, the temperature sensor operationally coupled to the motor, and the temperature sensor communicatively coupled to the controller; and
    wherein when the controller senses the parameter indicative of resection, the controller configured to sense temperature of the motor being above a predetermined threshold, the sensing by way of the temperature sensor.

6. The system of claim 5 wherein the controller further is configured to return to the first outflow rate if temperature of the motor falls below the predetermined threshold.

7. The system of claim 1:
    wherein the MDU further comprises a vibration sensor within the MDU, the vibration sensor operationally coupled to the motor, and the vibration sensor communicatively coupled to the controller; and
    wherein when the controller senses the parameter indicative of resection, the controller configured to sense vibration being above a predetermined threshold, the sensing by way of the vibration sensor.

8. The system of claim 7 wherein the controller is further configured to return to the first outflow rate if vibration falls below the predetermined threshold.

* * * * *